United States Patent
Kajiki

(10) Patent No.: US 10,980,503 B2
(45) Date of Patent: Apr. 20, 2021

(54) X-RAY FLUOROSCOPIC IMAGING APPARATUS

(71) Applicant: SHIMADZU CORPORATION, Kyoto (JP)

(72) Inventor: Shunsuke Kajiki, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 324 days.

(21) Appl. No.: 16/197,918

(22) Filed: Nov. 21, 2018

(65) Prior Publication Data

US 2019/0175134 A1 Jun. 13, 2019

(30) Foreign Application Priority Data

Dec. 11, 2017 (JP) .................. 2017-236792

(51) Int. Cl.
*A61B 6/00* (2006.01)
*G06T 5/00* (2006.01)

(52) U.S. Cl.
CPC ............ *A61B 6/5282* (2013.01); *A61B 6/487* (2013.01); *A61B 6/5258* (2013.01); *G06T 5/002* (2013.01); *G06T 5/008* (2013.01); *G06T 2207/10121* (2013.01); *G06T 2207/20208* (2013.01); *G06T 2207/30004* (2013.01)

(58) Field of Classification Search
CPC ..... A61B 6/5282; A61B 6/5258; A61B 6/487; A61B 6/5205; G06T 5/002; G06T 5/008; G06T 2207/30004; G06T 2207/10121; G06T 2207/20208; G06T 5/50; G06T 2207/20021; G06T 2207/20224; G06T 2207/10116; G06T 2207/10081; H04N 5/32

See application file for complete search history.

(56) References Cited

U.S. PATENT DOCUMENTS

2017/0086770 A1* 3/2017 Morita .................. A61B 6/025
2017/0231593 A1* 8/2017 Fukuda ............... A61B 6/5241
382/132

FOREIGN PATENT DOCUMENTS

JP 2017-35204 2/1917

* cited by examiner

*Primary Examiner* — Marcus Hammonds
(74) *Attorney, Agent, or Firm* — Andrew F. Young, Esq.; Nolte Lackenbach Siegel

(57) ABSTRACT

An X-ray fluoroscopy imaging apparatus that corrects to precisely remove a banding artifact in an X-ray image, includes an image processing unit that corrects an X-ray image by processing the image to remove the banding artifact (AF) from the X-ray image based on the average difference brightness value (DLa) relative to a plurality of pixels included in an array in an artifact extending direction (A-direction).

9 Claims, 9 Drawing Sheets

No banding artifact

Banding artifact is present

Any X-ray image without the banding artifact

One of X-ray image with the banding artifact

Flow-chart of the correction processing to remove the banding artifact from the X-ray image

X-RAY FLUOROSCOPIC IMAGING APPARATUS

CROSS REFERENCE TO RELATED APPLICATIONS

This application relates to, claim priority from, JP 2017-236792 filed Dec. 11, 2017, the entire contents of which are incorporated herein by reference.

FIGURE SELECTED FOR PUBLICATION

FIGS. 8A, 8B

BACKGROUND OF THE INVENTION

Field of the Invention

The present invention relates to an X-ray fluoroscopic imaging apparatus.

Description of the Related Art

Conventionally, it is known that there is an X-ray fluoroscopy imaging apparatus that executes an image processing to remove a band-artifact (e.g., refer to Patent Document 1).

Patent Document 1 discloses an X-ray fluoroscopy imaging apparatus that comprises an image averaging circuit that generates an average pixel value profile by averaging pixel values in the direction in which the banding (streaking) artifact is extending, and an approximation curve generation circuit that calculates an approximation curve that approximates the average pixel value profile further comprising: The above X-ray fluoroscopy imaging apparatus disclosed in Patent Document 1 further comprises a difference value calculation circuit that calculates a difference between the value of the average pixel value profile and the approximation curve, and an image correction circuit that corrects the X-ray image by subtracting the difference value from perspective pixel values relative to the X-ray image (executing a process to remove banding artifact from the X-ray image).

RELATED PRIOR ART DOCUMENTS

Patent Document

Patent Document 1: —JP 2017-35204

ASPECTS AND SUMMARY OF THE INVENTION

Objects to be Solved

However, according to the X-ray imaging apparatus of Patent Document 1, the X-ray image is corrected based on the difference value between the value of the average pixel value profile and the approximation curve approximating the average pixel value profile, so that the banding artifact is likely not removed satisfactorily when the calculation accuracy of the approximation curve is low. Therefore, correction to well accurately remove the banding artifact relative to the X-ray image may not be achieved.

The present invention has been proposed in order to solve the aforementioned problems, and an object of the present invention is to provide an X-ray imaging apparatus that can easily and absolutely measure a distance.

Means for Solving the Problem

To achieve the above purpose, an X-ray fluoroscopic imaging apparatus according to the one aspect of the present invention comprises: an irradiation element that irradiates X-ray to a subject; a detection element that detects the X-ray that irradiated to the subject; an image processing unit that generates an X-ray image based on the X-ray detection signal detected by the X-ray detection element; and a calculation circuit that calculates a difference brightness value that is a difference between brightness values relative to X-ray images and an average difference brightness value that is an average of the difference brightness values between X-ray images relative to a plurality of pixels included in the row of the artifact extending direction, in which the banding artifact occurring in the X-ray image are extending, wherein the image processing unit corrects the X-ray image by processing the image to remove the banding artifact from the X-ray image based on the average difference brightness value. In addition, the banding artifact is an artifact extending in the orthogonal direction to the read-out direction of the X-ray detection signal detected by the detection element (detector). In addition, the banding artifact is not limited to the artifact having some width in the read-out direction and broadly includes such as a line artifact consisting of only one pixel in the read-out direction.

The X-ray fluoroscopy imaging apparatus, according to the aspect of the present invention, as set forth above, the image processing unit corrects the X-ray image by processing the image to remove the banding artifact from the X-ray image based on the average difference brightness value relative to a plurality of pixels included in the array (line) of the artifact extending direction. Therefore, the banding artifact is removed based on the average difference brightness value between actual X-ray images reflecting the variation of the brightness value due to the banding artifact occurring by an array unit in the artifact extending direction. As a result, differently from the case using the approximate curve, the correction to remove the banding artifact in the X-ray image is achieved precisely by the image processing based on the value reflecting directly the actual variation amount of the brightness value due to the banding artifact.

According to one aspect of the X-ray fluoroscopic imaging apparatus as set forth above, it is preferable that the image processing unit corrects the X-ray image by subtracting the average difference brightness value from the brightness value of each pixel in the X-ray image. According to such a structure, the average difference brightness value reflecting the variation amount of the brightness value between the X-ray images occurring due to the banding artifact, is subtracted as-is from the brightness value between X-ray images. Therefore, correction to well accurately remove the banding artifact relative to the X-ray image may not be achieved.

According to one aspect of the X-ray fluoroscopic imaging apparatus set forth above, it is preferable that the image processing unit corrects the X-ray image by subtracting the average difference brightness value from the brightness value of each pixel in the X-ray image. According to such a structure, the number of pixels averaging for the average difference brightness value is maximized in the artifact extending direction. As a result, compared to the case based on the average difference brightness value obtained by averaging the relative smaller number of pixels, the effect of an error is suppressed, and the accuracy of the correction is improved.

According to one aspect of the X-ray fluoroscopic imaging apparatus set forth above, it is preferable that the calculation circuit determines whether correction of the X-ray image in the image processing unit is needed or not based on the (second) average difference brightness value averaging the (first) average difference brightness value in the area of the X-ray image including at least a plurality of arrays in the orthogonal direction to the artifact extending direction from the brightness value of each pixel in the X-ray image. According to such a structure, the impact to the (second) average difference brightness value is suppressed when the position of the subject varies between X-ray images in the orthogonal direction to the artifact extending direction in the area including at least the plurality of arrays by averaging the average difference brightness value in the area including a plurality of arrays in the orthogonal direction to the artifact extending direction. As a result, it is preciously determined whether the banding artifact is present or not and whether correction is needed or not.

In such a case, the calculation circuit determines whether correction of the X-ray image in the image processing unit is needed or not based on the (second) average difference brightness value averaging the (first) average difference brightness value in the entire of the X-ray image including all arrays in the orthogonal direction to the artifact extending direction. According to such a structure, the (first) area averaging the (second) average difference brightness value is maximized in the orthogonal direction to the artifact extending direction, so that the impact relative to the average difference brightness value is suppressed when the position of the subject varies between X-ray images in the orthogonal direction to the artifact extending direction.

According to one aspect of the X-ray fluoroscopic imaging apparatus set forth above, it is preferable that the calculation circuit calculates the average brightness value obtained by averaging the brightness values of the X-ray image and in addition, converts the average difference brightness value to the benchmark value to evaluate a degree of the impact of the banding artifact on the average brightness value depending on the difference between the subjects, and the image processing unit corrects the X-ray image based on the benchmark value. Here, the transmittance of the X-ray varies depending on the subject, so that the average brightness value of the X-ray image varies in accordance with such as difference between the subjects in the X-ray image and so forth. In addition, the visibility level (impact level) of the banding artifact in the X-ray image varies depending on the scale of the average brightness value. Therefore, according to the above structure, the X-ray image is correctable while considering the impact of the banding artifact relative to the average brightness value based on the benchmark value, so that the image processing unit corrects only when the correction is needed due to the large impact of the banding artifact. As a result, when the correction effect is lesser due to that the impact of the banding artifact is small, the correction by the image processing unit is suppressed.

In such a case, preferably, the calculation circuit calculates the benchmark value based on the ratio between the average difference brightness value and the average brightness value. According to such a structure, the ratio between the average difference brightness value corresponding to the variation of the brightness value due to the banding artifact and each average brightness value different corresponding to the difference between the subjects is applied to the benchmark value to evaluate the impact of the banding artifact. As a result, the impact level of the banding artifact relative to the average brightness value depending the difference between the subjects is easily evaluated.

With regard to the X-ray fluoroscopic imaging apparatus according to the aspect as set forth above, it is preferable that the calculation circuit calculates the average difference brightness value between the first X-ray image and the second X-ray image that is the X-ray image generated prior to the first X-ray image, the image processing unit corrects the first X-ray image based on either the second X-ray image in which it is determined that no banding artifact occurs or the second X-ray image in which it is determined that the banding artifact occurs, but the correction is already executed. According to such a structure, comparing with the case in which the banding artifact occurs in the second X-ray image, the impact of the banding artifact occurs assuredly to the average difference brightness value, so that correction for the first X-ray image to remove the banding artifact is assuredly executed.

In such a case, the image processing unit corrects the first X-ray image based on either the second X-ray image in which it is determined that no banding artifact occurs or the second X-ray image in which it is determined that the banding artifact occurs, but the correction is already executed and the latest updated second X-ray image. According to such a structure, the X-ray image, in which a variation of the position of the subject between X-ray images occurring over time is relatively small, is specified as the benchmark second X-ray image. Consequently, comparing with the case, in which the X-ray image has a relatively large variation of the position of the subject between X-ray images occurring is the reference second X-ray image, correction of the first X-ray image to remove the banding artifact based on the average difference brightness value further reflecting the variation of the brightness value due to the banding artifact is further assuredly executed.

Effect of the Invention

According to the aspect of the present invention, as set forth above, the present invention provides an X-ray fluoroscopy imaging apparatus that can accomplish the correction that precisely remove the banding artifact in the X-ray image.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
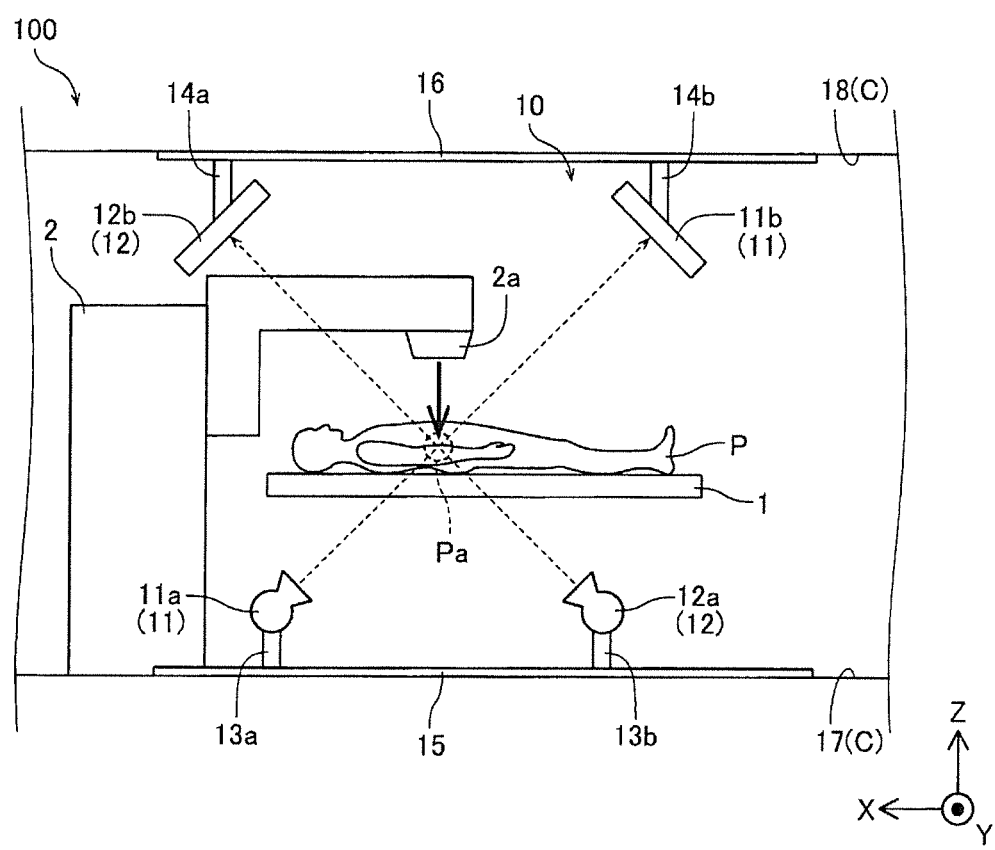
FIG. 1 is a view illustrating an entire structure of a radiotherapy tracking apparatus having an X-ray fluoroscopy imaging device according to the aspect of the Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner.

It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

The inventor sets forth specific Embodiments of the present invention based on the following FIGs.

Embodiment

First, referring now to FIG. 1, the inventor illustrates a radiotherapy tracking apparatus 100 comprising an X-ray fluoroscopic imaging apparatus 10 according to the aspect of the Embodiment 1 of the present invention.

(Structure of the Radiotherapy Tracking Apparatus)

Referring to FIG. 1, the radiotherapy tracking apparatus 100 according to the aspect of the present Embodiment is installed in an examination room C. The radiotherapy tracking apparatus 100 comprises a table 1 that loads a subject P, a radiotherapy radiation device 2 that irradiated a high-intensity radiation to the subject P and an X-ray fluoroscopy imaging apparatus 10 that performs an X-ray fluoroscopy or X-ray imaging on the subject P.

The radiotherapy radiation device 2 is the device that performs the radiotherapy with a relatively high-intensity radiation (indicated by a thick arrow in FIG. 1) being irradiated toward an affected area Pa of the subject P. The radiotherapy radiation device 2 comprises a radiotherapy radiation source 2a capable of irradiating the relatively strong radiation compared to the X-ray fluoroscopy imaging apparatus 10.

The radiotherapy tracking apparatus 100 tracks (dynamic-tracks) the affected area Pa of the subject P which moves along with a breathing and a beat, by the X-ray fluoroscopy using the X-ray fluoroscopy imaging apparatus 10. And, according to the radiotherapy tracking apparatus 100, the radiotherapy radiation device 2 irradiates the high-intensity radiation (for the therapy) toward the affected area Pa while adjusting the radiation position to the affected area Pa by dynamic tracking.

[System of an X-Ray Fluoroscopic Imaging Apparatus]

Figure 2:
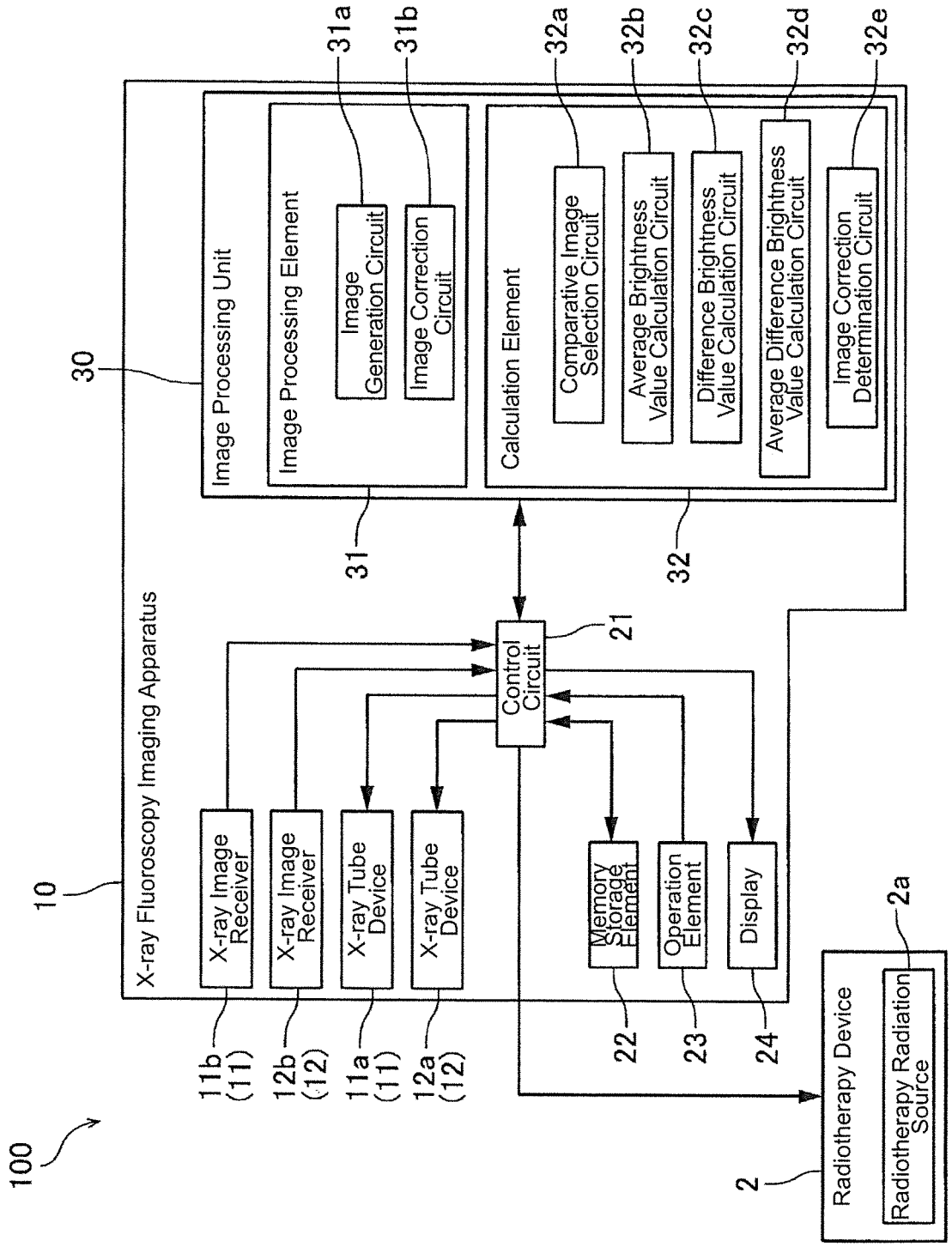
FIG. 2 is a block diagram illustrating a control system of the radiotherapy tracking apparatus having an X-ray fluoroscopy imaging device according to the aspect of the Embodiment 1.

Next, referring to FIG. 1 and FIG. 2, the inventor sets forth the system of the X-ray fluoroscopy imaging apparatus 10 according to the aspect of the Embodiment of the present invention.

Referring to FIG. 1, the X-ray fluoroscopy imaging apparatus 10 comprises the imaging system 11 including the X-ray tube device 11a and the X-ray image receiver 11b; the imaging system 12 including the X-ray tube device 12a and the X-ray image receiver 12b; the mount 13a, 13b; the mounts 14a, 14b; the rail 15; and the rail 16. In addition, the X-ray tube device 11a and 12a are an example of an "irradiation element" in claims. Further, the X-ray image receiver 11b and 12b are an example of a "detection element" in claims.

The X-ray tube device 11a and 12a are the device to irradiate an X-ray toward the subject P. The X-ray tube device 11a and 12a comprises the X-ray radiation source and is capable of irradiating an X-ray when an electric voltage is added by an X-ray tube driving element, not shown in FIG.

The X-ray image receiver 11b and 12b are the device to detect the X-ray irradiated toward the subject P. The X-ray image receiver 11b and 12b respectively detect the X-ray irradiated from the X-ray tube device 11a and 12a and convert the detected X-ray to the electric signal (X-ray detection signal). The X-ray image receiver 11b and 12b are, for example, an FPD (flat panel detector).

The X-ray image receivers 11b, 12b comprise a plurality of conversion elements (not shown in FIG.) and pixel electrodes (not shown in FIG.) placed on a plurality of the conversion elements. The plurality of conversion elements and the pixel electrodes are aligned in the two-dimensional matrix with a predetermined cycle (pixel pitch). The X-ray detection signal read out by the X-ray image receivers 11b, 12b is output to the image processing unit 30 (referring to FIG. 2) through the control circuit 21 (referring to FIG. 2). In addition, the read-out direction (referring to FIG. 3) of the X-ray detection signal relative to the X-ray fluoroscopy imaging apparatus 10 is R-direction (referring to FIG. 3).

The mounts 13a, 13b are respectively supporting the X-ray tube devices 11a, 12a. The mounts 13a, 13b change the angle of the X-ray tube devices 11a, 12a relative to the mounts 13a, 13b to enable adjustment of the irradiation direction of the X-ray.

The mounts 14a, 14b are respectively supporting the X-ray image receiver 11b, 12b. The mounts 14a, 14b change the angle of the X-ray image receivers 11b, 12b relative to the mounts 14a, 14b to enable adjustment of the direction of the X-ray detection surface.

The rail 15 is installed on the floor surface 17 of the examination room C. The rail 15 has an approximately U-shape rail (not shown in FIG.) to guide the mounts 13a, 13b in the X-direction and the Y-direction. Relative to the rail 15, the X-ray tube devices 11a, 12a move in the horizontal direction along the rail through the mounts 13a, 13b. In addition, in FIG. 1, the direction in which the subject P is lying is the horizontal direction (X-direction and Y-direction) and the vertical direction orthogonal thereto is Z-direction.

The rail 16 is installed to the ceiling surface 18 of the examination room C. The rail 16 has an approximately U-shape rail (not shown in FIG.) to guide the mounts 14a, 14b in the X-direction and the Y-direction. Relative to the rail 16, the X-ray image receivers 11b, 12b move on the XY-plane along the rail through the mounts 14a, 14b.

In addition, referring to FIG. 2, the X-ray fluoroscopy imaging apparatus 10 further comprises a control element 21, a memory storage element 22, an operation element 23, a display 24 and an image processing unit 30.

The control element 21 is a computer comprising a CPU (central processing unit), ROM (read only memory) and RAM (random access memory) and so forth. The CPU executes the predetermined control program, so that the control element 21 is operative to control each unit of the X-ray fluoroscopic imaging apparatus 10. In addition, the control element 21 also enables controlling the control element (not shown in FIG.) included in the radiotherapy radiation device 2 to irradiate the radiation from the radiotherapy radiation source 2a.

The memory storage element 22 comprises a memory device such as e.g., a hard disk drive. The memory storage element 22 stores: the control program that the control circuit 21 executes, the imaging processing program 16 that the image processing device 30 executes, and so forth. The memory storage element 22 stores the X-ray images 40 (referring to FIG. 3) generated or corrected by the image generation element 30. The memory storage element 22 stores the information of the X-ray image 40 such as the data with or without correction, the imaging (correction) date and so forth coordinating with the X-ray image 40.

The operation element 23 comprises, for example, a joy stick, a keyboard, a mouse, or other controller and so forth. The control element 21 receives the operation input through the operation element 23.

The display 24 is a monitor such as e.g., a liquid crystal display and so forth. The control element 21 controls the display element 24 to display the X-ray image 40 that the image processing unit 30 generates or corrects.

The image processing unit 30 is operative as an image processing unit by executing the image processing program stored in the memory storage element 22. The image processing unit 30 enables generation and correction of the X-ray image 40.

(Image Processing Device Configuration)

Next, the inventor sets forth the structure of the image processing unit 30 referring to FIG. 2-FIG. 8.

Referring to FIG. 2, the image processing unit 30 generates the X-ray image 40 by converting the X-ray detection signal output from the X-ray image receiver 11b, 12b seriatim to the brightness value L (referring to FIG. 4) corresponding to the intensity of the X-ray detection signal relative to the corresponding pixel 40a (referring to FIG. 3) every pixel 40a. The image processing unit 30 further comprises an image processing element 31 and a calculation element 32.

The image processing element 31 is a computer comprising processors such as a GPU (graphic processing unit) and an FPGA (field-programmable gate array) structured for image processing. The image processing element 31 further comprises the image generation circuit 31a and the image correction circuit 31b.

The image generation circuit 31a generate the X-ray images 40 by the predetermined frame rate by imaging the detection signals that the X-ray image receivers 11b, 12b output seriatim. Such frame rate is e.g., approximately in the range of 15 FPS to 30 FPS. The X-ray image 40 is an image having e.g., a pixel value (brightness value) L (referring to FIG. 4) of the predetermined gradation number (10-12 bits) in a gray-scale.

The image correction circuit 31b corrects the X-ray image 40 by processing the image to remove the banding artifact AF (referring to FIG. 3) from the X-ray image 40.

Figure 3:
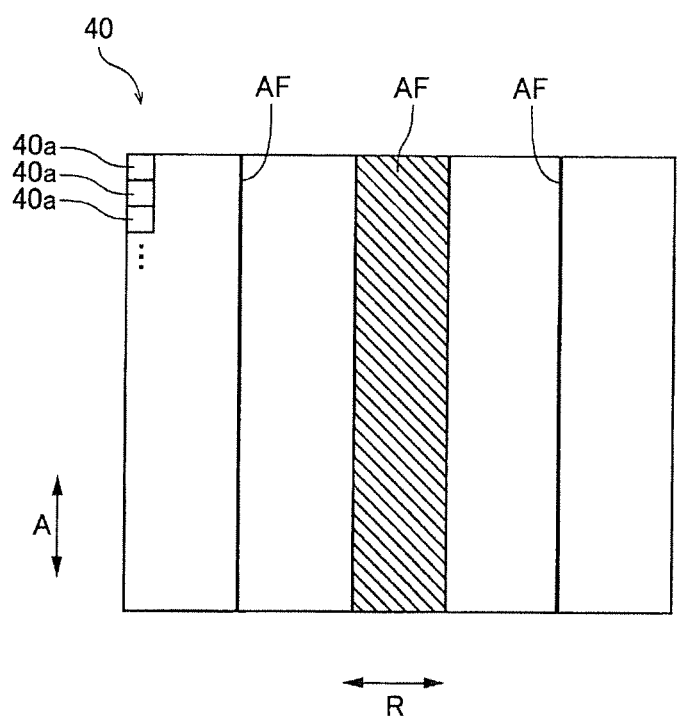
FIG. 3 is a schematic view illustrating an X-ray image in which a banding artifact occurs.

Referring to FIG. 3, the banding artifact AF is the banding artifact that occurs in the X-ray image 40 in the A-direction (artifact extending direction) orthogonal to the R-direction. The banding artifact AF occurs due to the difference between the scattering radiation amounts (due to the radiation irradiated from the radiotherapy radiation device 2) that are different based on the time-difference when the X-ray detection signal is read out.

Figure 4A:
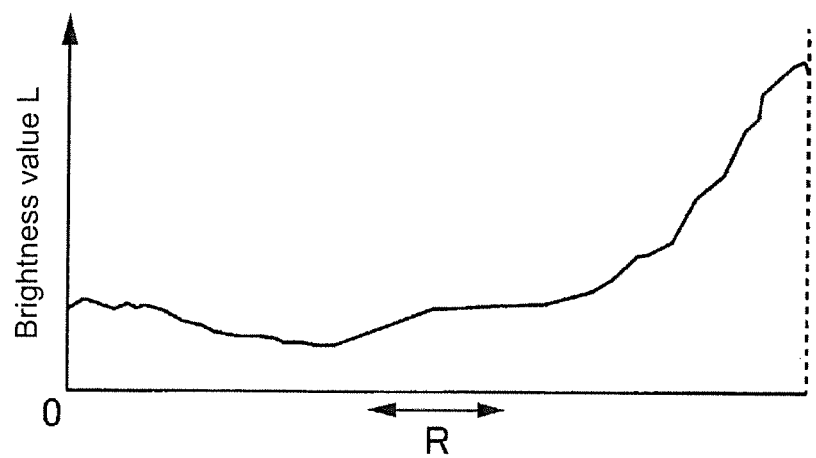
FIG. 4A is a brightness value profile in the read-out direction of the X-ray detection signal of the X-ray image without a banding artifact.
Figure 4B:
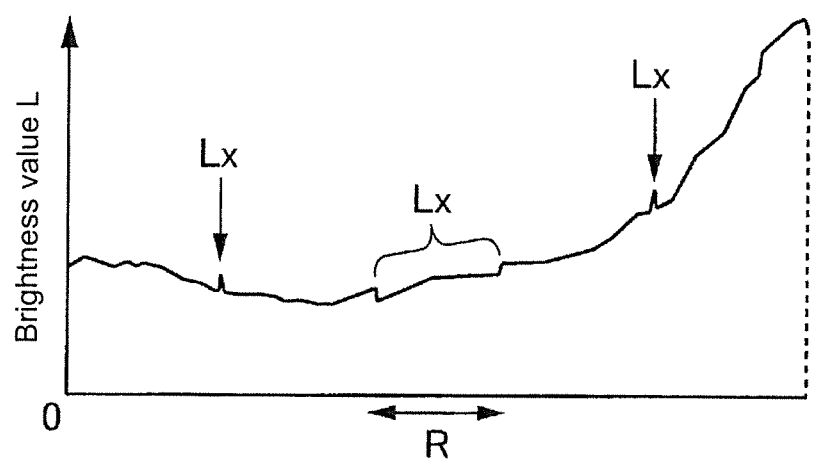
FIG. 4B is a brightness value profile in the read-out direction of the X-ray detection signal of the X-ray image with a banding artifact.

Here, when the banding artifact AF occurs in the X-ray image 40, the brightness value profile is as illustrated in FIG. 4B. In the brightness value profile illustrated in FIG. 4B, the brightness values L along the R-direction compared to the brightness value profile in the X-ray image 40 illustrated in FIG. 4A, in which no banding artifact AF occurs, are different allover, and also the abnormal variation Lx of the brightness value L at the specific position (at which the banding artifact AF occurs) in the R-direction. In addition, referring to FIG. 4A, 4B, the brightness value profile in the R-direction is obtained by plotting the average brightness value La (referring to FIG. 5), which is an average of brightness values L in all pixels 40a arrayed in the A-direction every array in the R-direction, along the R-direction. In addition, the impact of the scattering radiation relative to the X-ray fluoroscopy imaging apparatus 10 reaches all over the X-ray image 40, so that the brightness values L are likely different allover along the R-direction between the case when the banding artifact AF occurs in the X-ray image 40 (referring to FIG. 4B) and the case when no banding artifact AF occurs in the X-ray image 40 (referring to FIG. 4A).

The image correction circuit 31b corrects the X-ray image 40 based on the brightness value L of each pixel 40a (referring to FIG. 3) in the X-ray image 40 and the average difference brightness value DLa (referring to FIG. 8) every array extending in the A-direction and arraying in the R-direction. Specifically, the image correction circuit 31b corrects the X-ray image 40 by subtracting the average difference brightness value DLa every array extending in the A-direction corresponding to each pixel 40 from the brightness value L of each pixel 40a in the X-ray image 40. In addition, the calculation element 32 calculates the average difference brightness value DLa.

The calculation element 32 is a computer comprising a CPU (central processing unit), ROM (read only memory) and RAM (random access memory) and so forth. The control element 32 comprises a comparative image selection circuit 32a, an average brightness value calculation circuit 32b, a difference brightness value calculation circuit 32c, an average difference brightness value calculation circuit 32d and an image correction determination circuit 32e.

The comparative image selection circuit 32a selects an X-ray image 42 (referring to FIG. 6) that is the X-ray image 40 to be the comparative reference relative to the X-ray image 41 (referring to FIG. 6) that is the X-ray image 40 that determines necessity of correction. The X-ray image 42 is the X-ray image 40 having the (older and past) frame generated prior to the X-ray image 41. The X-ray image 41 is, for example, the newest (present) X-ray image 40 among the X-ray images 40 that are generated at the predetermined frame rate. In addition, the X-ray image 41 and the X-ray image 42 are respectively examples of the first X-ray image and the second X-ray image in claims.

Comparative image selection circuit 32a determines whether meeting the following two conditions as a selection condition to select the X-ray image 42 or not. The first condition is that the X-ray image 40 was determined in the past by the image correction determination circuit 32e as the banding artifact AF occurred or did not, or the X-ray image 40 was already corrected by the image correction circuit 31b even though the image correction determination circuit 32e determined (in the past) that the banding artifact AF occurred, or was not corrected yet. In addition, the second condition is that such an X-ray image is the newest X-ray image 40 among the X-ray images 40 meeting the first condition.

Figure 5:
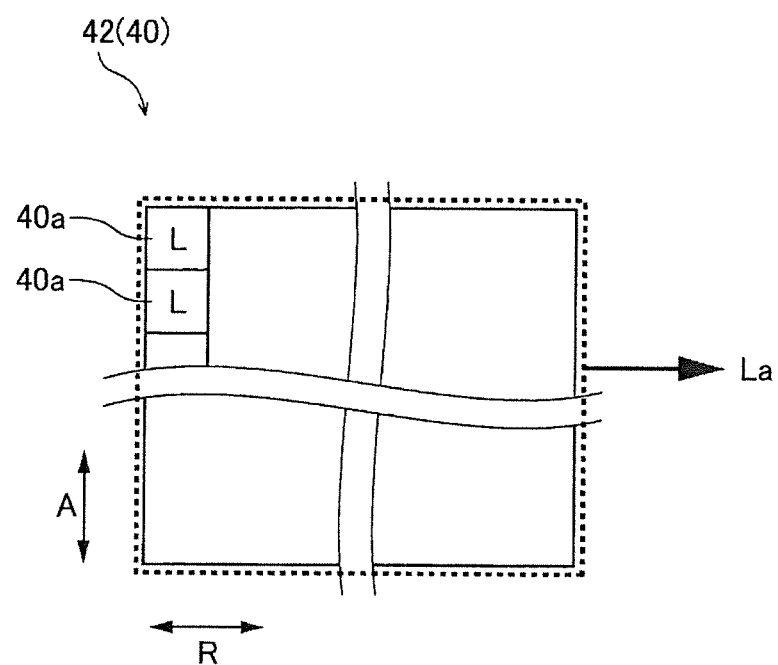
FIG. 5 is an explanatory view illustrating a calculation of the average brightness value in the X-ray image.
Figure 6:
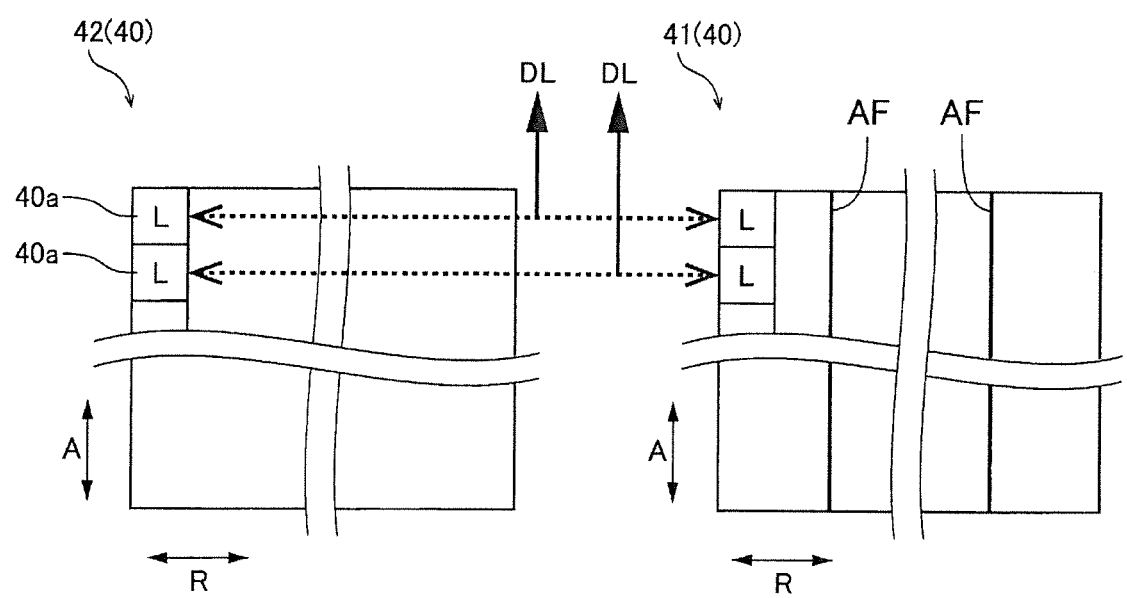
FIG. 6 is an explanatory view illustrating a calculation of the difference brightness value every pixel between X-ray images.

The average brightness value calculation circuit 32b calculates the average brightness value La (referring to FIG. 5) by averaging the brightness values L of a plurality of the pixels 40a in the X-ray image 40. Referring to FIG. 5, the average brightness value calculation circuit 32b calculates the average brightness value La of all X-ray images 40 (all pixels 40a of all X-ray images) relative to the X-ray image 40.

The difference brightness value calculation circuit 32c calculates the difference brightness value DL (referring to FIG. 6) that is the difference between the brightness values of respective X-ray images 40 every pixel 40a. Specifically, referring to FIG. 6, the difference brightness value calculation circuit 32c calculates the difference brightness value DL every pixel 40a between the predetermined pixel 40a of the X-ray image 41 and the pixel 40a corresponding to the X-ray image 42 that is generated prior to the X-ray image 41.

Figure 7A:
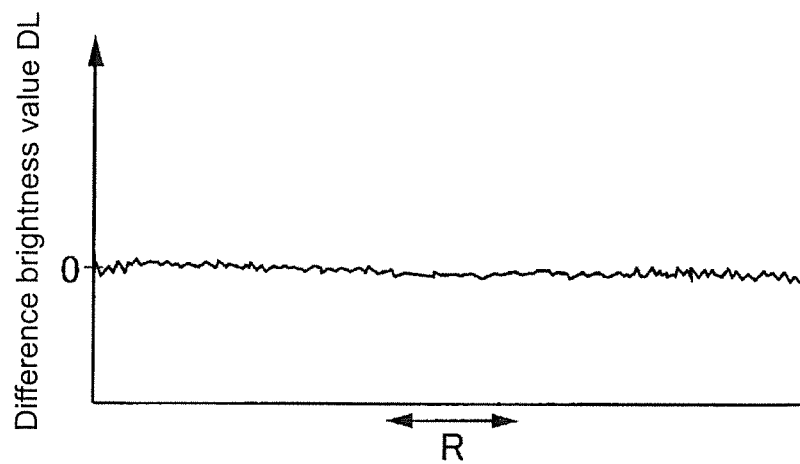
FIG. 7A is a difference brightness value profile in the read-out direction of the X-ray detection signal of the X-ray image without a banding artifact.
Figure 7B:
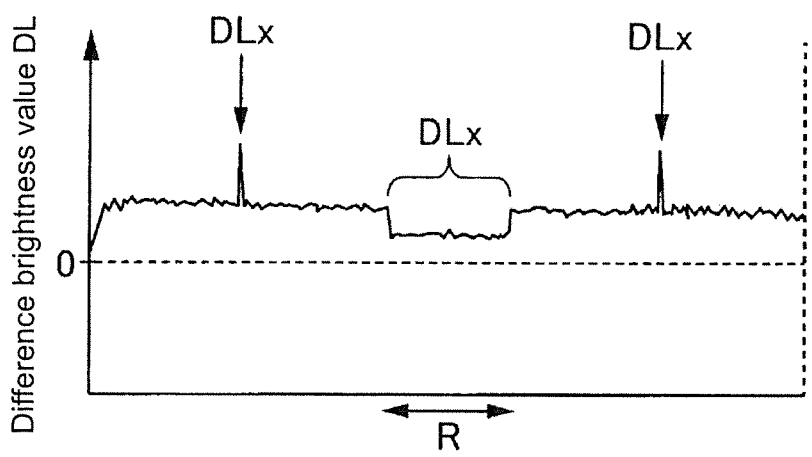
FIG. 7B is a brightness value profile in the read-out direction of the X-ray detection signal of the X-ray image with a banding artifact.

Here, the difference brightness value profiles in the R-direction based on the difference brightness value DL between the X-ray image 42 and the X-ray image 41, which is calculated by the difference brightness value calculation circuit 32c using the X-ray image 40 (41) having the brightness value profiles indicated in FIG. 4A and FIG. 4B, are respectively as illustrated in FIG. 7A and FIG. 7B. Here, when the banding artifact AF occurs in the X-ray image 41, the difference brightness value profile is as illustrated in FIG. 7B. In the brightness value profile illustrated in FIG. 7B, the different brightness values DL along the R-direction compared to FIG. 7A illustrating the difference brightness value profile using the X-ray image 41, in which no banding artifact AF occurs, are different overall and also the abnormal variation DLx of the difference brightness value DL occurs at the specific position (at which the banding artifact AF occurs) in the R-direction. Such a specific position is the same position as the position at which the abnormal variation Lx of the brightness value relative to the brightness value profile illustrated in FIG. 4B. In addition, referring to FIG. 7A, 7B, the brightness value profile in the R-direction is obtained by plotting the average difference brightness value DLa (referring to FIG. 8), which is an average of difference brightness values DL in all pixels 40a arrayed in the A-direction every array in the R-direction, along the R-direction.

Figure 8A:
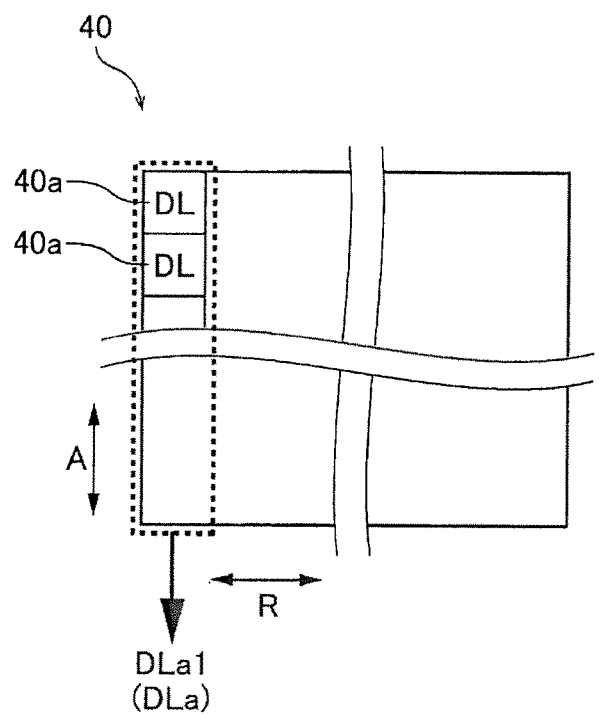
FIGS. 8A, 8B show explanatory views illustrating a calculation of the average difference brightness value between X-ray images.
Figure 8B:
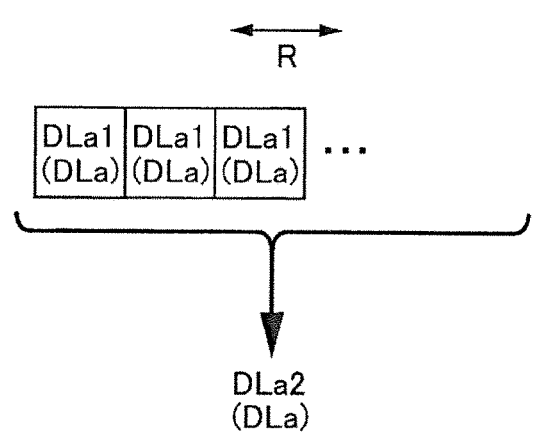

The average difference brightness value calculation circuit 32d calculates the (first) average difference brightness value DLa (referring to FIG. 8A, 8B) that is obtained by averaging the difference brightness value DL, which is calculated by the difference brightness value calculation circuit 32c, by a plurality of the pixels 40a in the X-ray image 40. Referring to FIGS. 8A, 8B, the average difference brightness value calculation circuit 32d calculates the (first) average difference brightness value DLa1 (referring to FIG. 8A) every array in the A-direction in the X-ray image 40, and the (second) average difference brightness value DLa2 (referring to FIG. 8B) of all X-ray images 40, which is obtained by further averaging the average difference brightness value DLa1 every array, i.e., dividing the value of the total of DLa1 by the number of Dla2, in the R-direction.

Here, the difference brightness value DL (average difference brightness value DLa) is a near null value (zero) approximately all over the difference brightness value profiles (referring to FIG. 7A) using the X-ray image 41, in which no banding artifact AF occurs. On the other hand, the difference brightness value DL (average difference brightness value DLa) is far from null value (zero) due to the scattering radiation in the specific position (position, at which no abnormal variation DLx occurs) in the R-direction in which no banding artifact AF occurs, relative to the difference brightness value profile (referring to FIG. 7B) of the X-ray image 41, in which the banding artifact AF occurs. On the other hand, with regards to the specific position (position, at which an abnormal variation DLx occurs) in the R-direction in which the banding artifact AF occurs, relative to the difference brightness value profile (referring to FIG. 7B) using the X-ray image 41, in which the banding artifact AF occurs, the difference brightness value DL (average difference brightness value DLa) is too far value, either large or small, from the difference brightness value DL (average difference brightness value DLa) of the specific position in the R-direction, in which no banding artifact AF occurs.

Therefore, when the X-ray image 41, in which no banding artifact AF occurs, is used, the difference brightness value DL (average difference brightness value DLa) is a near null value (zero), so that the average difference brightness values DLa1, DLa2 are near null (zero) value. On the other hand, when the X-ray image 41, in which banding artifact AF occurs, is used, the average difference brightness values DLa1, DLa2 are likely far from null value (zero).

The image correction determination circuit 32e determines necessity of correction of the X-ray images 40 based on the benchmark value calculated from the average difference brightness value DLa2 of all X-ray images 40, which the average difference brightness value calculation circuit 32d calculates, and the average brightness value La of all X-ray images 40, which the average brightness value calculation circuit 32b calculates. The image correction determination circuit 32e determines, for example, that when the benchmark value is larger than the pre-set predetermined threshold value, the correction is necessary, and when the benchmark value is smaller than the pre-set predetermined threshold value, the correction is unnecessary. The predetermined threshold value is set up by the user through the operation element 23 or is stored in advance in the memory storage element 22 in advance, e.g., on shipping the X-ray fluoroscopy imaging apparatus 10. In addition, the predetermined threshold value can be obtained from the data and so forth based on the average difference brightness value DLa2 of the past X-ray images 40 and the average brightness value La thereof.

The image correction determination circuit 32e uses the ratio (DLa2/La) between the average brightness value La of all X-ray images 40 and the average difference brightness value DLa2 of all X-ray images 40 as the benchmark value.

In addition, the benchmark value (DLa2/La) is the benchmark for evaluating the impact level of the banding artifact AF relative to the average brightness value La depending the difference between the subjects. And, the image correction determination circuit 32e determines that when the benchmark value (DLa2/La) is less than the predetermined threshold value, the difference brightness value DL is near null (zero), no banding artifact AF occurs in the X-ray image 41, and no correction of the X-ray image 40 is necessary. On the other hand, the image correction determination circuit 32e determines that when the benchmark value (DLa2/La) is larger than the predetermined threshold value, the difference brightness value DL is far from null (zero), the banding artifact AF occurs in the X-ray image 41, and correction of the X-ray image 40 is necessary.

In addition, when the impact level of the banding artifact AF in the X-ray image 41 is relatively small even when the banding artifact AF occurs in the X-ray image 40, the image correction determination circuit 32e determines that no correction of the X-ray image 40 is necessary. In detail, with regard to the X-ray image 40 of the subject P, having the average brightness value La of 500 due to that the X-ray hardly transmits, and the X-ray image 40 of the Subject P, having the average brightness value La of 5000 due to that X-ray easily transmits, given the average difference brightness value DLa2, including the impact of the banding artifact AF, is 30, the benchmark value (DLa2/La) is respectively 0.06 (=30/500) and 0.006 (30/5000). Therefore, the X-ray image 40 of the subject P having the average brightness value La of 5000 has relatively less impact level of the banding artifact AF compared to the X-ray image of the subject P having the average brightness value La of 500. Accordingly, with regard to the X-ray fluoroscopy imaging apparatus 10, when the benchmark value (DLa2/La) is less than the predetermined threshold value, the impact of the banding artifact AF is relatively small in the X-ray image 40, so that it is determined that no correction of the X-ray image 40 is necessary.

And, the X-ray image 41 that is determined by the image correction determination circuit 32e to be corrected is corrected by the image correction circuit 31b.

For example, with regard to the X-ray image 41 in which the banding artifact AF occurs, the image correction determination circuit 32e corrects by subtracting the average difference brightness value DLa every array in the A-direction corresponding to each pixel 40a from the brightness value L of each pixel 40a in the X-ray image 41. Here, the average difference brightness value DLa relative to (all pixels 40a included in the array extending in the A-direction corresponding to) the specific position in the R-direction, in which the abnormal variation Lx (banding artifact AF) of the brightness value L occurs, is getting far from null (zero) and largely distant value in either larger or smaller direction compared to the average difference brightness value DLa at the specific position in the R-direction in which no abnormal variation Lx (banding artifact AF) of the brightness value L occurs. Specifically, the average difference brightness value DLa at the specific position in the R-direction, in which the abnormal variation Lx (banding artifact AF) of the brightness value L, is deemed as the variation amount of the brightness value L due to the impact of the banding artifact AF. Therefore, with regard to all pixels 40a included in the array extending in the A-direction corresponding to the specific position in the R-direction at the specific position in the R-direction in which the abnormal variation Lx of the brightness value L occurs, the impact of the banding artifact AF is reduced by subtracting the average difference brightness value DLa every array in the A-direction corresponding to the respective pixels 40a from the brightness value L of each pixel 40a. Consequently, all over the entire X-ray images 40, the abnormal variation Lx of the brightness value L due to the banding artifact AF, referring to FIG. 4B, is suppressed (reduced) by correction, the correction is achieved to be the situation near the case, referring to FIG. 4A, in which no banding artifact AF occurs.

According to such an above structure, the image processing unit 30 corrects the X-ray image 40 by processing the image to remove the banding artifact AF from the X-ray image 40.

(Flow for the Correction Processing of the X-Ray Image)

Figure 9:
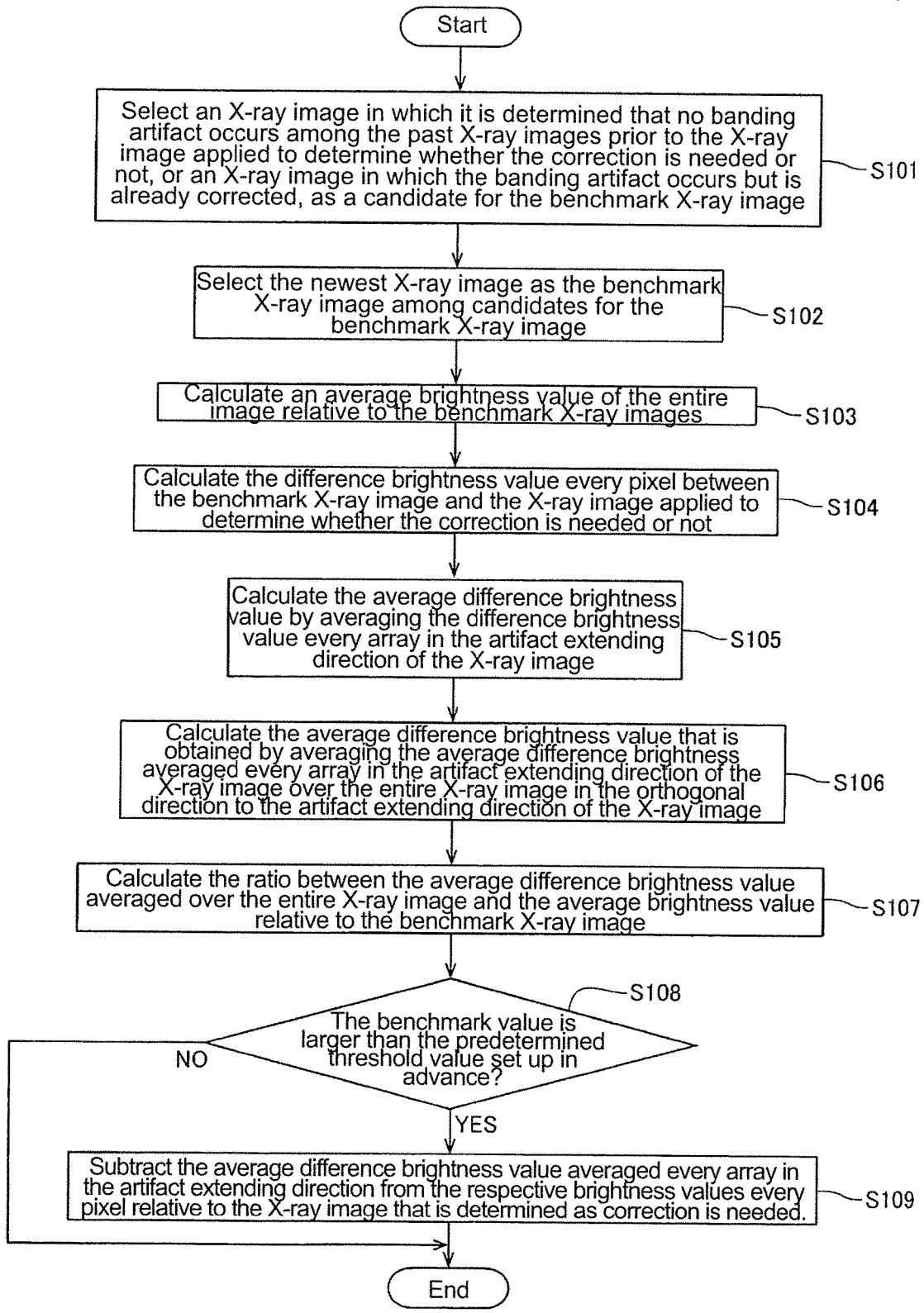
FIG. 9 is a flow-chart illustrating a correction processing to remove the banding artifact from the X-ray image.

Next, referring to FIG. 9, the inventors set forth a flow-chart illustrating the correction processing to remove the banding artifact AF from the X-ray image 40. In addition, it is given that the X-ray image 40 is already generated by the image generation circuit 31a (image processing element 31) before beginning the flow.

First, at the step S101 and the step S102, the comparative image selection circuit 32a (calculation element 32) selects the X-ray image 42 to be a comparative reference, which is generated prior to the X-ray image 41 relative to the X-ray image 41 that determines necessity of correction.

Specifically, at the step S101, the comparative image selection circuit 32a selects the X-ray image 40 for which the image correction determination circuit 32e determines that no banding artifact AF occurred (in the past) or the X-ray image 40 was already corrected by the image correction circuit 31b even though the image correction determination circuit 32e determined (in the past) that the banding artifact AF occurred, as a candidate for the X-ray image 42.

And, at the step S102, the comparative image selection circuit 32a selects the newest X-ray image 40 among the candidates of the X-ray image 42 selected at the step S101 as the reference X-ray image 42 to correct the X-ray image 41.

Next, at the step S103, the average brightness value calculation circuit 32b (calculation element 32) calculates the average brightness value La of all images relative to the reference X-ray image 42.

Next, at the step S104, the average difference brightness value calculation circuit 32c (calculation element 32) calculates every pixel 40a, the difference brightness value DL between the reference X-ray image 41 and the X-ray image 42 that determines necessity of correction.

Next, at the step S105, the average difference brightness value calculation circuit 32d (calculation element 32) calculates the average difference brightness value DLa1 (DLa) that is obtained by averaging the difference brightness values DL, which is calculated by the difference brightness value calculation circuit 32c, every array in the artifact extending direction (A-direction) in the X-ray image 40.

Next, at the step S106, the average difference brightness value calculation circuit 32d (calculation element 32) calculates the average difference brightness value DLa2 (DLa) that is obtained by averaging the average difference brightness values DLa1 (DLa) averaged every array in the artifact extending direction (A-direction) in the X-ray image 40 by all X-ray images 40 in the orthogonal direction (R-direction) to the artifact extending direction in the X-ray image 40.

Next. at the step S107, the image correction determination circuit 32e (calculation element 32) calculates the ratio (DLa2/La) between the average brightness value La of all X-ray images 40 and the average difference brightness value DLa2 of all X-ray images 40 as the benchmark value that evaluates the impact level of the banding artifact AF in the X-ray image 40.

Next, at the step S108, the image correction determination circuit 32e determines whether the value (DLa2/La) calculated as the benchmark value is larger than the preset predetermined threshold value or not. And, when it is determined that the value (DLa2/La) is larger than the predetermined threshold value, proceed to the step S109. In addition, when it is determined that the value (DLa2/La) is not larger than the predetermined threshold value, the correction of the X-ray image 42 is not executed and the correction processing flow ends.

Next, at the step S109, the image correction circuit 31b (image processing unit 31) corrects the X-ray image 41 by subtracting the average difference brightness value DLa1 averaged every array in the artifact extending direction (A-direction) from each brightness value L every pixel 40a of the X-ray image 41 that determines necessity of correction. According to such an above structure, the banding artifact AF is removed from the X-ray image 41.

(Effect According to the Aspect of the Present Embodiment)

The following effect can be obtained according to the aspect of the present Embodiment.

According to the aspect of the present Embodiment, as set forth above, the image processing unit 31 corrects the X-ray image 40 by processing the image to remove the banding artifact AF from the X-ray image 40 based on the average difference brightness value DLa relative to a plurality of pixels 40a included in the array in the artifact extending direction (A-direction). Therefore, the banding artifact AF is removed based on the average difference brightness value DLa between the actual X-ray images 40 reflecting the variation of the brightness value L due to the banding artifact AF occurring by an array unit in the artifact extending direction. As a result, differently from the case using the approximate curve, the correction to remove the banding artifact AF in the X-ray image 40 is achieved precisely by the image processing based on the value reflecting directly the actual variation amount of the brightness value due L to the banding artifact AF.

In addition, according to the aspect of the present Embodiment, the image processing unit 31 corrects the X-ray image 40 by subtracting the average difference brightness value DLa from the brightness value L of each pixel 40a in the X-ray image 40. According to such a structure, the average difference brightness value DLa reflecting the variation amount of the brightness value L between the X-ray images 40 occurring due to the banding artifact AF is subtracted as-is from the brightness value L between X-ray images 40. Consequently, correction to remove well precisely the banding artifact AF relative to the X-ray image 40 is easily achieved.

According to the aspect of the present Embodiment, as set forth above, the image processing unit 31 corrects the X-ray image 40 based on the average difference brightness value DLa averaged every array in the artifact extending direction (A-direction). According to such a structure, the number of pixels 40a averaged for the average difference brightness value DLa is maximized in the artifact extending direction. As a result, compared to the case based on the average difference brightness value DLa obtained by averaging the relatively smaller number of pixels 40a, the impact of an error is suppressed, and the accuracy of the correction is improved.

According to one aspect of the present Embodiment, as set forth above, the calculation element 32 determines whether correction of the X-ray image 40 in the image processing unit 31 is needed or not based on the average difference brightness value DLa obtained by averaging the average difference brightness value DLa averaged in the area of the X-ray image 40 including at least a plurality of arrays in the orthogonal direction (A-direction) to the artifact extending direction (R-direction). According to such a structure, the impact to the average difference brightness value DLa is suppressed when the position of the subject varies between X-ray images 40 in the orthogonal direction to the artifact extending direction in the area including at least the plurality of arrays by averaging the average difference brightness value DLa in the area including a plurality of arrays in the orthogonal direction to the artifact extending direction. As a result, it is preciously determined whether the banding artifact AF is present or not and whether correction is needed or not.

According to one aspect of the present Embodiment, as set forth above, the calculation element 32 determines whether correction of the X-ray image 40 in the image processing unit 31 is needed or not based on the average difference brightness value DLa obtained by averaging the average difference brightness value DLa in all X-ray images 40 including all arrays in the orthogonal direction (A-direction) to the artifact extending direction (R-direction). According to such a structure, the area averaging the average difference brightness value s DLa is maximized in the orthogonal direction to the artifact extending direction, so that the impact relative to the average difference brightness value DLa is further suppressed when the position of the subject P varies between X-ray images 40 in the orthogonal direction to the artifact extending direction.

In addition, according to the aspect of the present Embodiment, as set forth above, the calculation element 32 calculates the average brightness value La obtained by averaging the brightness values L of the X-ray images 40 and in addition and converts the average difference brightness value DLa to the benchmark value to evaluate an impact level of the banding artifact AF on the average brightness value La depending on the difference between the subjects P, and the image processing unit 31 corrects the X-ray images 40 based on the benchmark value. Therefore, according to the above structure, the X-ray image 40 is correctable while considering the impact of the banding artifact AF relative to the average brightness value La based on the benchmark value, so that the image processing unit corrects only when the correction is needed due to the high-impact of the banding artifact AF. As a result, when the correction effect on the X-ray image 40 is lesser due to that the impact of the banding artifact AF is small, the correction by the image processing unit 31 is suppressed.

In addition, according to the aspect of the present Embodiment, as set forth above, the calculation element 32 calculates the benchmark value based on the ratio (DLa/La) between the average difference brightness value DLa and the average brightness value La. According to such a structure, the ratio (DLa/La) between the average difference brightness value DLa corresponding to the variation of the brightness value L due to the banding artifact AF and each average brightness value La that is different corresponding to the difference between the subjects P is applied to the benchmark value to evaluate the impact of the banding artifact AF. As a result, the impact level of the banding artifact AF relative to the average brightness value La depending on the difference between the subjects P is easily evaluated.

In addition, according to the aspect of the present Embodiment, the calculation element 32 calculates the average difference brightness value DLa between the X-ray image 41 and the X-ray image 42 that is the X-ray image 40 generated prior to the X-ray image 41, the image processing unit 31 corrects the X-ray image 41 based on either average difference brightness value DLa of the X-ray image 42 in which it is determined that no banding artifact AF occurs or the X-ray image 42 in which it is determined that the banding artifact AF occurred, but the correction therefor is already executed. According to such a structure, comparing with the case in which the banding artifact AF occurs, the impact of the banding artifact AF reaches assuredly to the average difference brightness value DLa, so that correction for the X-ray image 41 to remove the banding artifact AF is assuredly executed.

In addition, according to the aspect of the present Embodiment, as set forth above, the image processing unit 31 corrects the X-ray image 41 based on either the X-ray image 42, in which it is determined that no banding artifact AF occurs, or the X-ray image 42, in which it is determined that the banding artifact occurred, but the correction is already executed, and the newest X-ray image 42. According to such a structure, the X-ray image 40, in which the variation of the position of the subject P between X-ray images 42 occurring over time is relatively small, is specified as the benchmark X-ray image 42. Consequently, comparing with the case, the X-ray image 40 having a relatively large variation of the position of the subject P between X-ray images 40 is specified as the reference X-ray image 42, correction of the X-ray image 41 to remove the banding artifact AF is further assuredly executed based on the average difference brightness value DLa further reflecting the variation of the brightness value L due to the banding artifact AF.

Alternative Embodiment

In addition, the aspects of the disclosed Embodiments here are examples and not limited thereto in any points. The scope of the present invention is specified in the claims but not in the above description of the aspect of the Embodiments and all alternative (alternative examples) are included in the scope of the claims and equivalents thereof.

For example, according to the aspect of the present Embodiment, as set forth above, the image correction circuit 31b corrects the X-ray image 40 by subtracting the average difference brightness value DLa1 every array (which is averaged brightness value L of all pixels 40a included in the array) in the A-direction (artifact extending direction) corresponding to each pixel 40a from the brightness value L of each pixel 40a in the X-ray image 40, but the present invention is not limited thereto. According to the aspect of the present invention, the image correction element may subtract the average difference brightness value of the part of pixels included in the array in the artifact extending direction from the brightness value of each pixel in the X-ray image.

In addition, according to the aspect of the above Embodiment, the image correction determination circuit 32e (calculation element 32) determines necessity of correction of the X-ray image 40 based on the average difference brightness value DLa2 of all X-ray images 40, but the present invention is not limited thereto. According to the aspect of the present invention, for example, the image correction determination circuit (calculation element) may determine necessity of correction of the X-ray image based on the average difference brightness value of the area (a part of X-ray image) including a plurality of arrays in the X-ray image. In addition, for example, the image correction determination circuit (calculation element) may determine necessity of correction of the X-ray image based on the average difference brightness value every array. In addition, for example, the image correction determination circuit (calculation element) may determine necessity of correction of the X-ray image based on the average difference brightness value of a part of pixels included in the array of the artifact extending direction. In addition, in such a case, necessity of correction relative to the entire X-ray image may be determined or necessity of correction relative to the part of X-ray image (only the area or the area and the periphery of the area) may be determined.

In addition, according to the aspect of the above Embodiment, the image correction determination circuit 32e (calculation element) determines necessity of correction of the X-ray image 40 based on the ratio (DLa2/La) between the average difference brightness value DLa2 of allover the entire X-ray images 40 and the average brightness value La of all X-ray images 40, but the present invention is not limited thereto. According to the aspect of the present invention, the image correction determination circuit (calculation element) may determine necessity of correction of the X-ray image based on the average difference brightness value per se of all X-ray images. For example, the image correction determination circuit (calculation element) may determine to execute correction of the X-ray image when the average difference brightness value of all X-ray images is larger than the predetermined threshold value.

In addition, according to the aspect of the above Embodiment set forth above, the comparative image selection circuit 32a (calculation element) selects the X-ray image 40 for which the image correction determination circuit 32e determines that no banding artifact AF occurred (in the past) as the candidate of the X-ray image 42 (second X-ray image) to be a reference that is generated prior to the X-ray image 41 relative to the X-ray image 41 (the first X-ray image) that determines necessity of correction or the X-ray images 40 that were already corrected by the image correction circuit 31b even though the image correction determination circuit 32e determined (in the past) that the banding artifact AF occurred, but the present invention is not limited thereto. According to the aspect of the present invention, the comparative image selection circuit (calculation element) selects only the X-ray image for which the image correction determination circuit determines that no banding artifact occurred (in the past) as the second X-ray image to be the reference, and may not select the X-ray image that was already corrected by the image correction circuit (in the past) even though the image correction determination circuit determined (in the past) that the banding artifact AF occurred.

In addition, when the imaging region moves periodically, the comparative image selection circuit may select the X-ray image that is the X-ray image having the same phase (the positional relationship between the internal organs and the blood vessels of the subject coincides approximately with each other), the X-ray image that the image correction determination circuit determined (in the past) in which no banding artifact occurred, or the X-ray image that it was determined in which the banding artifact occurred (in the past), but the image correction circuit already is corrected, from the plurality of X-ray images of the periodically moving subject as a second X-ray image to be a reference. Consequently, even when the variation of the position of the subject between X-ray images occurring over time is relatively large, correction of the X-ray image to remove the banding artifact is further assuredly executed.

In addition, according to the aspect of the above Embodiment set forth above, the comparative image selection circuit 32a (calculation element) selects the X-ray image 40 for which the image correction determination circuit 32e determines that no banding artifact AF occurred (in the past) or the newest X-ray image 40 among the X-ray images 40 were already corrected by the image correction circuit 31b even though the image correction determination circuit 32e determined (in the past) that the banding artifact AF occurred, but the present invention is not limited thereto. According to the aspect of the present invention, the comparative image selection circuit may select the X-day image from any of the X-ray image that was determined in the past by the image correction determination circuit as no banding artifact occurred and the X-ray image that was already corrected by the image correction circuit even though the image correction determination circuit determined (in the past) that the banding artifact occurred.

In addition, according to the aspect of the Embodiment set forth above, the image processing unit 30 that generates and corrects the X-ray image 40 is installed separately from the control element 21 that controls each element of the X-ray fluoroscopy imaging apparatus 10, but the present invention is not limited thereto. According to the aspect of the present invention, the image processing unit may be included in the control element. In addition, with regard to the image processing unit and the calculation element that the image processing device comprises, the control element may carry out the operation of the calculation element.

In addition, according to the aspect of the Embodiment set forth above, with regard to the radiotherapy tracking apparatus 100 comprising the radiotherapy radiation device 2 and the X-ray fluoroscopy imaging apparatus 10, the banding artifact in the X-ray image 40 is removed to correct the X-ray image 40, but the present invention is not limited thereto. The present invention is applicable to any structure in which a banding artifact occurs due to any impact of such as a scattering radiation relative to any X-ray fluoroscopy imaging apparatus carrying out the X-ray fluoroscopy or the X-ray imaging.

In addition, according to the aspect of the Embodiments set forth above, for convenience of explanation, the inventors set forth a flow of the flow driving processing in which the processing of the image processing unit 30 executes correction processing on the X-ray image 40 following the processing flow in order, but the present invention is not limited thereto. According to the present invention, the correction processing of the image processing unit can be performed using an event driving processing (event driven type) every event. In such case, a perfect event driven processing can be applied, or a combination of the event driven processing and flow driven processing can be applied.

REFERENCE OF SIGNS

10 X-ray fluoroscopy imaging apparatus
11a, 12a X-ray tube device (irradiation element)
11b, 12b X-ray image receiving element (detector)
31 Image processing unit
32 Calculation circuit
40 X-ray image
40a Pixel
41 X-ray image (first X-ray image)
42 X-ray image (second X-ray image)
AF Banding artifact
P Subject
L Brightness value
La Average brightness value
DL Difference brightness value
DLa (Dla1, DLa2) Average difference brightness value*

As used herein, a computer-type system comprises an input device for receiving data in any form, an output device for outputting data in any form (e.g., data stream, file record, imagery, printing or displaying on a computer screen etc.), a memory for storing data as well as computer code, and a processor/microprocessor for executing computer code wherein the computer code is resident in the memory and will cause the processor/microprocessor to read-in data via the input device, process the data within the processor/microprocessor and output the data processed data via the output device.

It will be further understood by those of skill in the art that the apparatus and devices and the elements herein, without limitation, and including the sub components such as operational structures, inter-linked circuits and individual circuits, and inter-linked modules and modules, and related communication pathways, and related elements, control elements of all kinds, display circuits and display systems and elements, and any and all necessary driving elements, inputs, sensors, detectors, memory elements, components, circuits, modules, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray fluoroscopic imaging apparatus systems and devices, computer and operational controls and technologies of radiographic devices and all their sub components, including various circuits, modules, and combinations of circuits and modules without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet as non limiting examples, and all other kinds of computers, systems, and computing platforms.

A processor/microprocessor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" as a specific quoted combination of means+for are intended to be interpreted under 35 USC 112. Use of the word 'means' is merely descriptive of a system, component, apparatus, circuit, module, aspect etc., such that it is merely a descriptive noun and does not and cannot trigger review under § 112. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray fluoroscopy imaging apparatus, comprising:
an irradiation element that irradiates a plurality of X-rays through a subject;
a detector that detects the plurality of X-rays that are irradiated through said subject;
said detector including a plurality of pixels included in an array positioned along an artifact extending direction in which a banding artifact occurring in an X-ray image extends;
an image processing unit that generates a plurality of X-ray images each based on an X-ray detection signal detected by said detector;
a calculation circuit that calculates a first difference brightness value for every pixel, which is a difference between brightness values relative to respective said X-ray images, and a second average difference brightness value which is an average of each respective said first difference brightness values between each said X-ray image relative to said plurality of pixels included in said array; and
wherein said image processing unit corrects each said X-ray image by processing each said X-ray image to remove said banding artifact from said X-ray image based on said second average difference brightness value.

2. The X-ray fluoroscopy imaging apparatus, according to claim 1, wherein:
said image processing unit corrects said X-ray image by subtracting said second average difference brightness value from said brightness value of each said pixel in said X-ray image.

3. The X-ray fluoroscopy imaging apparatus, according to claim 1, wherein:
said image processing unit corrects said X-ray image based on said second average difference brightness value averaged along said array in said artifact extending direction.

4. The X-ray fluoroscopy imaging apparatus, according to claim 1, wherein:
said calculation circuit determines a necessity of correction of said X-ray image in said image processing unit based on said second average difference brightness value obtained by averaging said first average difference brightness value in an area of said X-ray image including at least a plurality of arrays in an orthogonal direction to said artifact extending direction from the brightness value of each pixel in the X-ray image.

5. The X-ray fluoroscopy imaging apparatus, according to claim 4, wherein:
said calculation circuit determines said necessity of correction of said X-ray image in said image processing unit based on said second average difference brightness value obtained by averaging said first average difference brightness value in an entire area of said X-ray image including all arrays in the orthogonal direction to said artifact extending direction.

6. The X-ray fluoroscopy imaging apparatus, according to claim 1, wherein:
said calculation circuit calculates a second average brightness value obtained by first averaging said brightness values of said X-ray image and converts said second average difference brightness value to a benchmark value to evaluate an impact level of said banding artifact on said second average brightness value depending on a difference between said subjects, and
said image processing unit corrects said X-ray image based on said benchmark value.

7. The X-ray fluoroscopy imaging apparatus, according to claim 4, wherein:
said calculation circuit calculates said benchmark value based on a ratio between said second average difference brightness value and said average brightness value.

8. The X-ray fluoroscopy imaging apparatus, according to claim 1, wherein:
said calculation circuit calculates said second average difference brightness value between a first X-ray image and a second X-ray image that is said X-ray image generated prior to said first X-ray image, said image processing unit corrects said first X-ray image based on at least one determination selected from a group consisting of a first determination, wherein said second X-ray image has no banding artifact and a second determination, wherein said second X-ray image is corrected even though a banding artifact occurs therein.

9. The X-ray fluoroscopy imaging apparatus, according to claim 1, wherein:
said image processing unit corrects said first X-ray image based on a newest image of said second images and at least one said second X-ray image selected from a group consisting of said second X-ray image, wherein no said banding artifact occurs therein and said second X-ray image, wherein said second X-ray image is corrected even though said banding artifact occurs therein.

* * * * *